United States Patent [19]

Wiegand et al.

[11] 4,187,230

[45] Feb. 5, 1980

[54] PREPARATION OF 5-AROYL-PYRROLE COMPOUNDS

[75] Inventors: Karl E. Wiegand; James T. F. Kao; Michael J. Dagani, all of Baton Rouge, La.

[73] Assignee: Ethyl Corporation, Richmond, Va.

[21] Appl. No.: 848,936

[22] Filed: Nov. 7, 1977

Related U.S. Application Data

[63] Continuation of Ser. No. 580,761, May 27, 1975, abandoned, which is a continuation-in-part of Ser. No. 480,009, Jun. 17, 1974, abandoned.

[51] Int. Cl.² .................. C07D 207/32; C07D 409/06
[52] U.S. Cl. ..................... 260/326.47; 260/326.5 J; 260/326.35

[58] Field of Search ............... 260/326.5 J, 326.47, 260/326.35

[56] References Cited

U.S. PATENT DOCUMENTS 3,846,447  11/1974  Carson .................. 260/326.47

Primary Examiner—Alton D. Rollins
Assistant Examiner—Mary C. Lee
Attorney, Agent, or Firm—Donald L. Johnson; John F. Sieberth; James M. Pelton

[57] ABSTRACT

A process for acylating pyrrole compounds comprising reacting an aroyl halide with the pyrrole compound in the presence of an alkyl aluminum halide. Such acylated pyrrole derivatives are useful as intermediates for the preparation of anti-inflammatory agents and as synthetic intermediates.

23 Claims, No Drawings

PREPARATION OF 5-AROYL-PYRROLE COMPOUNDS

CROSS REFERENCE TO RELATED APPLICATION

This application is a continuation of application Ser. No. 580,761, filed May 27, 1975, now abandoned, which in turn is a Continuation-in-Part of application Ser. No. 480,009, filed June 17, 1974, now abandoned.

BACKGROUND OF THE INVENTION

This invention relates to the production of 5-aroyl-pyrrole compounds. Such compounds are known and described in U.S. Pat. No. 3,752,826 to Carson. According to the teaching of Carson, compounds such as 5-aroyl-pyrrole alkanoic acids and the corresponding salts, esters, nitriles, amides and substituted amides are prepared by Friedel-Crafts reaction between an appropriate aroyl halide (I), preferably chloride, and a pyrrole-2-acetic acid derivative (II), such as the cyano or lower alkoxy-carbonyl, in the presence of a Lewis acid, preferably a metallic halide, such as aluminum chloride to form 5-aroyl-pyrrole-2-acetic acid derivatives (III). The reaction of Carson is shown in the following schematic diagram:

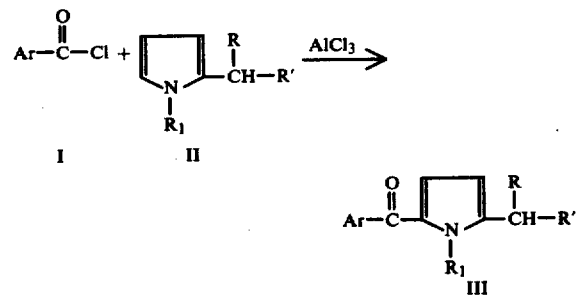

in which Ar represents a member selected from the group consisting of phenyl, thienyl, 5-methylthienyl mono-substituted phenyl and poly-substituted phenyl, each substituent of said substituted phenyls being a member selected from the group consisting of halo, lower alkyl, trifluoromethyl, lower alkoxy, nitro, amino, cyano and methylthio; R represents a member selected from the group consisting of hydrogen and lower alkyl; $R_1$ represents a member selected from the group consisting of hydrogen, lower alkyl and benzyl, and R' is cyano or lower alkoxy-carbonyl. Suitable solvents are those typically employed in Friedel-Crafts reaction such as methylene chloride, 1,2-dichloroethane, carbon disulfide, nitrobenzene and the like. The 5-aroyl-pyrrole-2-acetic acid derivative (III) can then be converted to corresponding 2-carboxylic acid by conventional hydrolysis. For example, by heating a solution of the 5-aroyl-pyrrole-2-acetic acid derivative with an alkali metal hydroxide to form the alkali metal salt of the acid and then acidifying the mixture.

A wide variety of 5-aroyl-pyrroles are produced according to the process schemes shown in Carson. Such compounds have useful pharmacological properties which make them suitable for formulation in conventional pharmaceutical forms for administration. The 5-aroyl-pyrrole compounds described in Carson have been found to possess anti-inflammatory activity which has been demonstrated in standard kaolin-induced rat paw edema and cotton pellet granuloma tests at doses generally ranging from 5–100 mg/kg body weight. Accordingly, improved processes for acylating the pyrrole-2-acetic acid derivatives are desirable. Thus, it is an object of the present invention to provide a process for preparing 5-aroyl-pyrrole-2-acetic acid derivatives, and particularly 5-aroyl-pyrrole-2-acetonitrile, in higher yields, using a process providing advantages over the prior art. The foregoing and other objects are accomplished by the process of the present invention.

SUMMARY OF THE INVENTION

According to the present invention, there is provided a process for selectively acylating a pyrrole compound in a position alpha to the nitrogen atom and without alkylating the pyrrole nucleus, comprising reacting an aroyl halide and a pyrrole compound in the presence of an alkyl aluminum halide while maintaining the reaction mixture at a temperature of about 0° to about 40° C. Preferably, the pyrrole compound is a pyrrole-2-acetic acid derivative, for example, 1-methylpyrrole-2-acetonitrile. Further, preferred aroyl halides are toluoyl and benzoyl halides, for example, toluoyl chloride and benzoyl chloride. Typically, the alkyl aluminum halide compound can be dialkyl aluminum halide, alkyl aluminum dihalide and alkyl aluminum sesquihalide compounds, such as, ethyl aluminum dichloride, diethyl aluminum chloride, dimethyl aluminum chloride and ethyl aluminum sesquichloride.

DESCRIPTION OF PREFERRED EMBODIMENTS

According to the present invention there is provided a process for the preparation of 5-aroyl-1-methylpyrrole-2-acetonitrile compounds. Such compounds have a characteristic pyrrole ring structure in which various substituents are placed on the pyrrole ring according to the process of the present invention. Accordingly, a starting material which is necessary for the present invention is a pyrrole compound, such as, a 1-lower alkyl pyrrole compound, preferably a 1-methylpyrrole compound and, more preferably, a 1-methylpyrrole-2-acetic acid derivative as described hereinabove. The starting pyrrole compound may have various other substituents attached to the pyrrole ring structure. For example, in the 2-position groups selected from cyano, carboxy, carboxylic acid ester, amide, substituted amide, substituted diamide and similar groups can be attached via a methylene group. The pyrrole compound may also have substituted in the 3- and/or 4-position a radical which is a member of the group consisting of cyano, carboxylic acids, lower alkyl esters of carboxylic acids, amides of carboxylic acids, lower alkyl and di-lower alkyl substituted amides of carboxylic acids, lower alkyl amino alkylene amides of carboxylic acids and the like. In the 5-position, the present process can be used to attach an aroyl group, for example, toluoyl, benzoyl, p-chlorobenzoyl, thienoyl or similar groups having an aromatic nucleus which may be mono- or poly-substituted with lower alkyl, halo, cyano, nitro, lower alkoxy, amino, methylthio, trifluoromethyl and similar groups.

As used herein, the term "lower alkoxy" and "lower alkyl" means a straight or branched chain saturated hydrocarbon group having from 1–6 carbon atoms such as, for example, methyl, ethyl, propyl, isopropyl, butyl, pentyl, hexyl and similar alkyls and, respectively, the corresponding alkoxy groups such as methoxy, ethoxy, propoxy, isopropoxy, etc. Accordingly, preferred compounds produced by the process of this invention are 5-aroyl-1-methylpyrrole-2-acetic acid compounds. Most preferably, the compounds produced according to this process are 5-aroyl-1-methylpyrrole-2-acetonitrile compounds. Numerous examples of such compounds are known in the art and all of the 5-aroyl-pyrrole compounds disclosed in the Carson patent are hereby incorporated by reference as if fully set forth.

The starting material for the process of the present invention is a pyrrole compound, for example, a 1-lower alkyl pyrrole-2-acetonitrile, preferably 1-methylpyrrole-2-acetonitrile. As indicated above, the pyrrole ring may be substituted in the 3-and/or 4-position as well. However, for purposes of the present invention, the simpler 1-methylpyrrole-2-acetonitrile will be used for illustrative purposes.

The 1-methylpyrrole-2-acetonitrile is acylated with an aroyl halide. Appropriate aroyl halides can be the aroyl chloride iodide, bromide and fluoride with the aroyl chloride being illustrative and preferred. The aroyl group can be any of those indicated above. Accordingly, preferred aroyl groups are toluoyl, benzoyl, naphthoyl, p-chlorobenzoyl, p-toluoyl, p-nitrobenzoyl, 4-nitronaphthoyl, 5-propylthienoyl, m-isopropyltoluoyl, p-butylbenzoyl, 5-pentylnaphthoyl, p-hexylbenzoyl, p-methoxybenzoyl, p-ethoxybenzoyl, 4-propoxynaphthoyl, p-butoxybenzoyl, 5-pentyloxynaphthoyl, m-aminotoluoyl, 5-cyanothienoyl, p-trifluoromethylbenzoyl, p-methylthiobenzoyl, 5-chlorothienoyl, 3-bromobenzoyl, 3-fluoro-4-methylbenzoyl and the like.

Such aroyl halides are generally known and may be obtained by transformation of the corresponding acid of the acid chloride formed according to conventional procedures, such as refluxing of the aryl acid with thionyl chloride and distilling off excess thionyl chloride under vacuum to produce the corresponding aroyl chloride product.

According to such procedure, aroyl chlorides such as 3,4-dimethoxybenzoyl chloride, 3-bromo-4-chlorobenzoyl chloride, 2,3,5-tribromobenzoyl chloride, 3,4-dimethylbenzoyl chloride, p-ethylbenzoyl chloride, p-ethoxybenzoyl chloride and p-methylthiobenzoyl chloride may be produced. In the process of the present invention a preferred aroyl halide is p-toluoyl halide and most preferred is p-toluoyl chloride. The amount of aroyl chloride required is only that sufficient to react with the pyrrole compound, usually an equimolar amount or up to about a 5 weight percent excess is all that is necessary.

The aroyl halide and pyrrole derivative are reacted in the presence of an alkyl aluminum halide composition. Any suitable alkyl aluminum halide compound which does not adversely effect the product or reactants and gives a reasonable rate of reaction may be employed. Preferably, the alkyl group is a "lower alkyl" as defined hereinabove. Typical alkyl aluminum halide compounds are alkyl aluminum dihalides, dialkyl aluminum halides, alkyl aluminum sesquihalides and mixtures or other forms of these. Some examples of suitable dialkyl aluminum halides are:
dimethyl aluminum bromide,
diethyl aluminum bromide,
diethyl aluminum chloride
di-n-propyl aluminum chloride,
diisobutyl aluminum iodide,
diisoamyl aluminum chloride,
dihexyl aluminum chloride,
and the like. Examples of useful alkyl aluminum dihalides include:
methyl aluminum dichloride,
ethyl aluminum dichloride,
ethyl aluminum dibromide,
n-propyl aluminum dichloride,
isobutyl aluminum dibromide,
n-hexyl aluminum dibromide,
and the like. Both the dialkyl aluminum halides and the alkyl aluminum dihalides are believed to exist in the form of dimers and these, of course, are included within the scope of the present invention.

Alkyl aluminum sesquihalides having the formula $R_3Al_2X_3$, in which R represents an alkyl group, preferably a lower alkyl group, and X represents a halogen atom, are useful in the present invention. Examples of typical alkyl aluminum sesquihalides include:
methyl aluminum sesquichloride,
methyl aluminum sesquibromide,
ethyl aluminum sesquichloride,
ethyl aluminum sesquibodide,
ethyl aluminum sesquiiodide,
n-propyl aluminum sesquichloride,
n-propyl aluminum sesquibromide,
isobutyl aluminum sesquichloride,
isobutyl aluminum sesquiiodide,
n-hexyl aluminum sesquiiodide,
and the like.

The above alkyl aluminum halide compounds can be used individually or can be added as mixtures to the aroyl halide or to the reaction mixture with good results. Frequently, due to their tendency to ignite on exposure to air, the alkyl aluminum halides are used in the form of solutions in inert solvents such as hydrocarbons or ethers. Particularly useful solvents are the hydrocarbons such as hexane, heptane, isooctane, benzene, toluene, xylene and the like. However, in the present process a solvent is not necessary.

The use of an alkyl aluminum halide has several advantages. Increased yields, reaction at reasonable temperatures and reasonable reaction rates and cleaner reactions are several process advantages which can be mentioned. Pyrrole compounds are known to polymerize in the presence of acids. Without limiting the invention to any particular theory of mechanism of operation, it is believed that acids are produced on reaction of the aroyl halide with the pyrrole compounds forming a hydrogen halide which is reacted with an equivalent of alkyl aluminum halide to form an aluminum halide and evolve a hydrocarbon gas. Thus, by removing the hydrogen halide, polymerization of pyrrole is prevented, increasing yields and preventing formation of heavy ends in the reaction mixture.

Although alkyl aluminum halides are preferred, the process can also be carried out using aryl aluminum halides and, hence, these are considered equivalents. However, the alkyl aluminum halides are more readily available and are accordingly preferred. Most preferred are alkyl aluminum halides in which the alkyl groups are lower alkyl groups as defined hereinabove. Also,- most preferred are alkyl aluminum halides wherein halogen is chlorine. Thus, most preferred alkyl aluminum halides are selected from the group consisting of diethyl aluminum chloride, ethyl aluminum dichloride and ethyl aluminum sesquichloride. Most highly preferred is diethyl aluminum chloride. The amount of alkyl aluminum halide, as indicated above, is that sufficient to give reasonable rate of reaction. It has been found that a stoichiometric amount of the alkyl aluminum halide compound is preferred and a slight excess up to about 10 weight percent can be advantageous to obtain the best reaction.

The reaction can be carried out in a liquid, facilitating contact of the reactants which is substantially inert to the reactants and product and has sufficient solvent power for keeping reactants and products in suspension or solution. Such reaction medium or liquid diluent is preferably an organic compound from the group consisting of saturated paraffinic hydrocarbons, halogenated hydrocarbons, especially halogenated aliphatic and aromatic hydrocarbons. Typical examples are solvents which are suitable for Friedel-Crafts reactions such as, for example, methylene chloride, 1,2-dichloroethane, carbon disulfide, nitrobenzene and the like. Preferably, methylene chloride, dichlorobenzene and monochlorobenzene are employed. The amount of reaction medium required is not critical and an amount sufficient to maintain a stirrable reaction mixture can be employed. The use of a solvent is not critical, however, it provides process advantages in allowing good heat transfer without localized hot spots in the reaction and facilitates contact of the reactants. Preferably the reaction medium is an alkyl or aryl halide, most preferably, a lower alkyl halide such as methyl chloride, ethyl chloride, propyl chloride, isopropyl chloride, butyl chloride, pentyl chloride, hexyl chloride and the di- and, where possible, trichlorinated alkyls, or a mono-, di- or trichlorobenzene, toluene or xylene or analogs, bromides or mixed halides thereof. Most preferably, the reaction medium is methylene chloride, 1,2-dichloroethane or monochlorobenzene, with monochlorobenzene being most highly preferred.

The reaction is carried out at a temperature sufficient to obtain a good rate of reaction and yield within practical limitations of capital investment and process economics. Preferably, the reaction can be carried out at a temperature ranging from 0° to about 40° C. Although temperatures higher and lower than this can be employed, the more preferred reaction temperature range is from 5° to about 25° C. Initially, the reaction mixture may be frozen by, for example, using dry ice to obtain a reactant slush and the reactant mixture is then warmed up to reaction temperature. In the alternative, the reactants can be added to the reactor at the lower end of the reaction temperature range and as reaction proceeds the reactants are heated to the higher end of the reaction temperature range.

The reaction can be carried out for a time sufficient to obtain a good yield at reasonable reaction rates and with regard to reasonable cycle times. Practical considerations with respect to the size of equipment and capital investment should be taken into account when reaction times are determined. The reaction time is not critical and depends, for example, on the temperature of reaction, reactivity of reactants and the degree of completeness of reaction desired and minimization of side reactions. Preferably, the reactants are fed to the reactor for a period sufficient to obtain the desired conditions. The reaction mixture can be held at low temperatures, for example, less than 0° C. for an indefinite period without a significant amount of reaction. However, after allowing the reactor contents to warm up to a temperature sufficient for reaction, it proceeds for from about 30 to about 210 minutes, preferably from 90 to about 180 minutes. Best results are obtained when the reaction is allowed to occur over a period from about 90 to about 120 minutes and such times are more preferred.

As indicated above, the reactants can be mixed together at low temperature and then warmed to reaction temperature. Alternatively, a mixture of the aroyl chloride and pyrrole compound can be made and the alkyl aluminum halide added, either all at once or over a period of time, to this mixture at reaction temperature. Another alternative is to mix the pyrrole compound and alkyl aluminum halide with the reaction medium and then add thereto the aroyl chloride. At reaction temperature, an excess of one reactant or another could have effects on selectivity and yield of desired 5-aroyl pyrrole compound. Moreover, the addition of reactants and/or alkyl aluminum halide can be made all at once or one or more of the reactants may be added over a relatively short period of time, for example, from 15 to about 45 minutes, according to one of the alternate modes described hereinabove. Best results are obtained when the aroyl halide and pyrrole are mixed in a suitable reaction medium and the alkyl aluminum halide is added over a period of from about 30 to about 45 minutes.

After reaction has occurred, the starting alkyl aluminum halide has been converted to another aluminum compound having one more halide atom replacing an alkyl group, for example, diethyl aluminum chloride would be converted to ethyl aluminum dichloride, and a slight amount of alkyl aluminum halide may remain because of incomplete reaction or excess added. After reaction for a sufficient period of time to be substantially complete, the remaining alkyl aluminum halide is decomposed by a suitable decomposition agent and then the desired 5-acylated pyrrole compound can be recovered. Any suitable agent which decomposes alkyl aluminum halides can be used, typical are water, alcohols, dilute acids, bases and mixtures of these, for example, water can be used or lower alkanols such as methanol, ethanol, isopropanol and dilute inorganic mineral acid such as hydrochloric acid and the like. Preferred alkyl aluminum halide decomposition agents are water, isopropanol and dilute hydrochloric acid.

Another advantageous function of the alkyl aluminum halide decomposition agent is to form a separate phase into which the by-products of alkyl aluminum halide decomposition, e.g., aluminum hydroxide and/or aluminum chloride, will be removed from the organic phase containing the 5-aroyl pyrrole product. For this purpose, excess decomposition agent is employed. Preferably, from about 1 to about 2 moles or greater of decomposition agent based on the amount of alkyl aluminum halide may be used. Of course, larger excesses of decomposition agent may give more convenient decomposition rates and/or phase separations.

Generally, a typical procedure for conducting the process of the present invention includes the provision of a reactor fitted with temperature sensing means, stirrer and an overhead condenser. To the reactor is added the reaction medium, aroyl halide and the pyrrole compound. The mixture is then stirred and cooled to around 0° C. Then a sufficient amount of alkyl aluminum halide from an addition funnel is added over about a 45 minute period. The mildly exothermic reaction takes place and temperatures are controlled at 0°–40° C. during addition. The gas generated during reaction is vented. The reaction mixture is held with stirring at 10°–20° C. for from ½ to 3½ hours after addition. Very little gas is evolved during the last hour of holding. The color of the reaction mixture is reddish-brown. The last traces of alkyl aluminum halide are removed by one of the several methods indicated hereinabove. In another preferred embodiment, for example, the reaction mixture itself can be poured into water. The catalyst decomposition reaction is very exothermic during the first addition of reaction mixture into water. Cooling must be provided to control the temperature below 30° C. After slow addition of the first ¼ of the reaction mixture the remaining amount of reaction mixture can be added at a faster rate. The reaction mixture is allowed to separate into two layers, the bottom dark brown layer containing the product. The lower layer is removed and the solvent evaporated to give solid 5-aroyl substituted pyrrole.

According to the process of this invention, it is preferred to carry out the reaction in which the pyrrole compound is 1-methylpyrrole-2-acetonitrile. The preferred alkyl aluminum halide is diethyl aluminum chloride, and the preferred aroyl halide is p-toluoyl halide, most preferably p-toluoyl chloride. During the reaction, the reaction mixture is maintained at a temperature of from about 5° to about 25° C. and the reaction medium employed is methylene chloride. In a further preferred embodiment of the process of this invention includes the reaction for a period ranging from about 90 to about 120 minutes and then adding an amount of alkyl aluminum halide decomposition agent sufficient to decompose the remaining alkyl aluminum halide catalyst, for example, water, an alkanol or dilute acid, and recovering the 5-substituted aroyl pyrrole-2-acetonitrile from the reaction mixture.

The following examples are illustrative of the process of this invention. After examples of this invention, there are given some comparative experiments in which a metallic halide, e.g., aluminum chloride is used. Finally, several examples showing typical procedures for the process of this invention are given.

EXAMPLE 1

In a serum capped vial was placed 1.2 g (10 mmoles) of a nitrile mixture containing 90.8 mole % 1-methylpyrrole-2-acetonitrile and 9.2 mole % 1,2-dimethyl-5-cyanopyrrole and 1.55 g of p-toluoyl chloride (10 mmoles) in 10 ml of methylene chloride which had been dried over a molecular sieve. To this mixture was added 2.5 ml of a solution prepared by taking 6 g (11.8 mmoles) of ethyl aluminum dichloride and adding dry hexane to make 10 ml of solution. The initial nitrile-p-toluoyl chloride solution was frozen in a dry ice slush and then allowed to just thaw at which point the ethyl aluminum dichloride-hexane solution was added. The mixture was then allowed to warm up to room temperature over a period of ½ hour. As the temperature reached 15°–20° C., evolution of ethane began and continued for about 10 minutes. After a further 10 minutes elapsed, 2 ml of methanol was added and the mixture began to boil with the heat of reaction and/or ethane evolution. The reaction mixture was then treated with about 50 ml of dilute (about 5%) hydrochloric acid and the aqueous phase was extracted twice with methylene chloride. The extracts were combined, followed by drying over sodium sulfate, and gave 2.216 g of product after evaporation of the methylene chloride. This material was added to enough 1,2-dichloroethane to make a solution of 50 ml and a 5 ml aliquot was analyzed by vapor phase chromatography giving the following compositions:

Unknown—0.36%
1,2-Dimethyl-5-cyanopyrrole—3.45%
1-Methylpyrrole-2-acetonitrile—0%
Unknown—2.04%
5-p-Toluoyl-1-methylpyrrole-2-acetonitrile—51.40%
4-p-Toluoyl-1-methylpyrrole-2-acetonitrile—38.90%
Accountability—96.15%
Yield based on the starting nitrile content—92.4% of which 52.6% is the 5-acylnitrile and 39.8% is 4-acylnitrile Recovery of starting amount of 1,2-dimethyl-5-cyanopyrrole—69.2%

In a similar procedure as that of Example 1, several other alkyl aluminum halides and solvents were employed. The results are shown in Table I.

TABLE I

Acylation of 1-Methylpyrrole-2-acetonitrile with Alkyl Aluminum Halide

| Example | Alkyl Aluminum Halide | Solvent | Temp. Reaction Began, °C. | % Yield 5-p-Toluoyl-1-methylpyrrole-2-acetonitrile | % Yield 4-p-Toluoyl-1-methylpyrrole-2-acetonitrile |
|---|---|---|---|---|---|
| 2 | Di-isobutyl aluminum chloride | Methylene chloride | 25–30 | 44.8 | 25.2 |
| 3 | Di-isobutyl aluminum chloride | Chlorobenzene | 25–30 | 48.8 | 23.8 |
| 4 | Dimethyl aluminum chloride | Methylene chloride | ~ −5 | 62.7 | 34.8 |

The following procedure employs ethyl aluminum dichloride as the alkyl aluminum halide is added over a period of time instead of all in a single addition as in the previous example.

EXAMPLE 5

To a 1-liter, 4-necked flask reactor, fitted with thermometer, stirrer and overhead condenser, was added 150 g of methylene chloride, 39 g of p-toluoyl chloride (0.25 mole), 30 g of a mixture of pyrroles (93.3% 1-methylpyrrole-2-acetonitrile and 4.2% 1,2-dimethyl-5-cyanopyrrole, 0.25 mole total). The mixture was stirred and cooled to 10° C., 32 g (0.25 mole) of ethyl aluminum dichloride was then added over a 30 minute period with an addition funnel. Ethane gas was generated and vented. The reaction mixture was held with stirring at 10° for 30 minutes and then warmed to 21° C. and held for an additional 40 minutes. Then, approximately 250 g of water was added slowly with cooling to maintain the temperature below 30° C. The bottom organic phase was separated. It weighed 152 g and was analyzed by vapor phase chromatography. The analysis indicated that the yield of 5-p-toluoyl-1-methylpyrrole-2-acetonitrile was 48.7% based upon the starting nitrile and the ratio of the 5-p-toluoyl isomer to 4-p-toluoyl isomer was 1.5.

EXAMPLE 6

To a 500-ml, 4-necked glass reactor fitted with thermometer, stirrer and overhead condenser was added 150 g methylene chloride, 39 g p-toluoyl chloride (0.25 mole) and 40 g of a mixture of 1-methylpyrrole nitriles (93.3% of 1-methylpyrrole-2-acetonitrile and 4.2% of 1,2-dimethyl-5-cyanopyrrole, 0.243 moles total). The mixture was stirred and cooled to 7.5° C., 30 g (0.25 mole) of diethyl aluminum chloride in an addition funnel was then added over a 45-minute period. A mildly exothermic reaction was observed and temperature was controlled at 10° C. during addition. Ethane gas was generated and vented. The reaction mixture was held with stirring at 10° C. for 3.5 hours. Very little gas was evolved during the last hour of holding. The color of the reaction mixture was reddish-brown. Next, 220 g of water was added to decompose the remaining diethyl aluminum chloride. The reaction was very exothermic during the first few drops of water. Cooling was provided to control the temperature below 30° C. After slow addition of the first 25 ml of water, the remaining water was added at a faster rate. The mixture was siphoned out and allowed to separate in two layers. The bottom dark brown layer contained the product. It weighed 172.1 g of which 167 g were evaporated to give 57.1 g of brown solid.

The crude product solution was analyzed by vapor phase chromatography to give the following composition in weight percent:

Methylene chloride—61.25 (65.8 by evaporation)
1,2-Dimethyl-5-cyanopyrrole—0.62
1-Methylpyrrole-2-acetonitrile—0.30
5-Cyano-1,2-dimethyl-3-p-toluoylpyrrole—0.14
5-p-Toluoyl-1-methylpyrrole-2-acetonitrile—21.71
4-p-Toluoyl-1-methylpyrrole-2-acetonitrile—9.32
Miscellaneous unknowns—approximately 0.66
Total—93.86 (98.41 by evaporation)

Material balance calculations from the above analyses indicates that 90% of the 1,2-dimethyl-5-cyanopyrrole was recovered but only 1.7% of starting 1-methylpyrrole-2-acetonitrile was remaining in the crude product solution. The yield of 5-p-toluoyl-1-methylpyrrole-2-acetonitrile was 67.4% and the ratio of 5-p-toluoyl isomer to 4-p-toluoyl isomer was 2.3.

The effect of variation of the reaction time, temperature, addition time and the method of decomposing the remaining alkyl aluminum halide compound was studied by a procedure similar to Example 6. Table II below shows that the reaction temperature has important effects on yield. The effect of varying the method of hydrolysis of remaining alkyl aluminum halide has little effect on the results. Accordingly, the results of several experiments are shown in Table II hereinbelow:

TABLE II

| | Acylation of 1-Methylpyrrole-2-acetonitrile With Alkyl Aluminum Halide Catalyst Under Varied Reaction Conditions | | | | |
|---|---|---|---|---|---|
| Example number | 7 | 8 | 9 | 10 | 11 |
| Purity of 1-methylpyrrole-2-acetonitrile[1] | 93.3 | 93.3 | 93.3 | 93.3 | 93.3 |
| Alkyl aluminum halide[2] | DEAC | DEAC | DEAC | DEAC | DEAC |
| Temperature, °C. | 10 | 10 | 10 | 20 | 20 |
| Time, minutes | | | | | |
| Addition | 30 | 45 | 45 | 45 | 60 |
| Holding | 180 | 210 | 210 | 120 | 120 |
| Method of Alkyl Aluminum Halide Decomposition[3] | A | A | B | C | C |
| Results Based on VPC | | | | | |
| % of original 1-methylpyrrole-2-acetonitrile | 5.0 | 1.0 | 2.2 | 0 | 2.7 |
| % of original 1,2-dimethyl-5-cyanopyrrole | 80 | 41 | 88 | 71 | 93 |
| Yield of 5-p-toluoyl-1-methylpyrrole-2-acetonitrile | 56 | 64 | 65 | 67 | 1 |
| Ratio of 5-p-toluoyl isomer 4-p-tuluoyl isomer | 2.4 | 2.3 | 2.5 | 2.5 | 2.2 |

[1]4.2% 1,2-dimethyl-5-cyanopyroole
[2]DEAC - diethyl aluminum chloride
[3]Method of decomposition:
A. Add water to reaction mixture below 34° C.
B. Add isopropanol to the reaction mixture below 30° C., then add water.
C. Add reaction mixture to water below 20° C.

For comparative purposes, the procedure of Example 6 was repeated in which triethyl aluminum was employed as a catalyst. However, the reaction mixture became a solid mass on stirring after the addition of the triethyl aluminum could not be further stirred and the experiment was discontinued.

In a further comparative experiment following the procedures of Example 5, 30 g of a mixture of 1-methylpyrrole nitriles (90.7% 1-methylpyrrole-2-acetonitrile and 9.3% 1,2-dimethyl-5-cyanopyrrole mixture, 0.25 mole total) was mixed with 38.6 g (0.25 mole) of p-toluoyl chloride in 250 ml of methylene chloride. A slurry of 33.3 g of aluminum chloride and 250 ml of ethylene chloride was prepared and maintained suspended by stirring mechanically in a dropping funnel. The pyrrole-acid chloride mixture was cooled to −30° to −35° C. with dry ice slush and the aluminum chloride slurry added steadily over about ½ hour. The mixture was stirred magnetically becoming homogeneous in a short time. The mixture was then allowed to warm up to about 20° C. and a sample taken showed a substantial amount of unreacted p-toluoyl chloride by NMR analysis. Although the pyrrole protons were shifted, probably by a complexation with aluminum chloride, no appreciable exotherm was noted during the warming of the reaction mixture of 20° C. The reaction mixture was allowed to react for a total of 17 hours at room temperature after which a sample taken appeared completely reacted. The mixture was hydrolyzed with distilled water, about 250 ml, and phases separated. The aqueous phase was extracted twice with methylene chloride. The extracts were combined with the organic phase of the reaction mixture and these were dried with anhydrous sodium sulfate. The methylene chloride was evaporated on a steam bath leaving a residue of 70 g containing 16.67% methylene chloride by VPC. The crude product weight was by difference 58.33 g. Vapor phase chromatograph analysis of the crude product showed 37.95% of 5-p-toluoyl-1-methylpyrrole-2-acetonitrile and 25.98% 4-p-toluoyl-1-methylpyrrole-2-acetonitrile, which calculates to a yield of 49.2% of the 5-p-toluoyl isomer and 33.7% yield of 4-p-toluoyl isomer. The ratio of 5-p-toluoyl isomer to 4-p-toluoyl isomer was 1.46 and a total yield of only 83% of acylated pyrrole compared with isomer ratios of 2.2-2.5 and total yield of acylated pyrrole of 95 to 99% using the alkyl aluminum halide, such as diethyl aluminum chloride. Product accountability by VPC for this comparative experiment was 82.54%, the remainder being apparently aluminum compounds or heavy ends. The selectivity of the reaction was low in comparison to the reactions with alkyl aluminum chloride with respect to acylation of the 1,2-dimethyl-5-cyanopyrrole. Since only 11.2% of this starting impurity remains compared to about 93% with the alkyl aluminum halide reactions.

In another comparative experiment following as closely as possible Example XIII of Carson, U.S. Pat. No. 3,752,826, 26.6 g of anhydrous aluminum trichloride (0.20 mole) and 80 ml of 1,2-dichloroethane which had been dried over a molecular sieve were added to a reaction vessel and stirred together in a dry nitrogen atmosphere and then 30.9 g of p-toluoyl chloride (0.2 mole) was added to give a soluble complex while maintaining a temperature of approximately 25° C. using an ice bath. The resulting solution was transferred to a dropping funnel and added to a solution of 24.2 g (0.20 mole) of a pyrrole mixture (90.7 weight percent 1-methylpyrrole-2-acetonitrile and 9.3 weight percent 1.2-dimethyl-5-cyanopyrrole) in 80 ml of 1,2-dichloroethane over approximately 30 minutes while maintaining a temperature of 20° C. The resulting solution was stirred at room temperature for 20 minutes and then refluxed for 3 minutes. The solution was poured into ice acidified with dilute HCl and the mixture allowed to just melt. The lower organic layer was separated and combined with a chloroform extract of the upper aqueous phase and the mixture was washed successively with dilute 1,3-propanediamine, dilute hydrochloric acid, 5 percent aqueous sodium bicarbonate and saturated sodium chloride. The organic layer was then dried over anhydrous $Na_2SO_4$, filtered and the solvent stripped off to yield 56.45 g of stripped product.

On analysis by vapor phase chromatograph, the product contained 16.87 g of 5-p-toluoyl-1-methylpyrrole-2-acetonitrile plus 1,2-dimethyl-5-cyano-3-p-toluoyl pyrrole, 18.80 g of 4-p-toluoyl-1-methylpyrrole-2-acetonitrile and 0.067 g of 1,2-dimethyl-5-cyano pyrrole. Because of the limitations of the vapor phase chromatograph and the interference of 1,2-dimethyl-5-cyano-3-p-toluoyl pyrrole, the percentage of 5-p-toluoyl-1-methylpyrrole-2-acetonitrile was determined to be 29.1-31.58 percent. The yield of 4-p-toluoyl-1-methylpyrrole-2-acetonitrile was 43.5 percent. Yield of total acylated pyrrole compound was 74.85 percent.

It is clear that more of the 4-p-toluoyl-1-methylpyrrole-2-acetonitrile species was produced and the reaction is much less selective than the process of the present invention. This experiment followed as closely as possible Example XIII of Carson patent, U.S. Pat. No. 3,752,826, except for the use of impure 1-methylpyrrole-2-acetonitrile and washing with 1,3-propanediamine. However, such minor variations are not believed significant for comparison of the results with results from the examples of the present invention. Accordingly, it can be seen that the reaction in the presence of aluminum alkyl halide is more selective, produces higher yields and gives a better reaction than with aluminum chloride according to the prior art.

A typically employed procedure of the instant process can be illustrated in the following manner.

EXAMPLE 12

A glass-lined reactor fitted with agitator, cooling water jacket, temperature sensing means, vent lines, and reactant feed and product discharge lines was purged with nitrogen for 15 minutes. Then 275 pounds of methylene chloride was added to the reactor and the agitator and brine coolant flow in the water jacket were started. Then 71 pounds of p-toluoyl chloride and 55 pounds of a mixture of 1-methylpyrrole-2-acetonitriles (usually containing as an impurity 1,2-dimethyl-5-cyano pyrrole) were successively added to the reactor. The agitator speed was increased, the reactor contents were cooled to 10° C. and, after purging the feed line with nitrogen, 55 pounds of diethyl aluminum chloride was added at a rate of 0.1 gpm over a period of about 50 minutes while maintaining the reaction mixture at about 20° C. Because of gas evolution during the reaction the diethyl aluminum chloride should be added with the reactor vent line open. The reaction mixture was stirred for 2 hours while the temperature was maintained at 20° C. Then a stainless steel reactor also having an agitator, cooling water jacket, charge and discharge lines, vent line and temperature sensing means was filled with 385 pounds of demineralized water. The agitator was started and cooling set at 10° C. Then after the reaction mixture from the first reactor reacted for 2 hours at 20° C. it was transferred to the second reactor over a period of about 60 minutes. The addition of reaction mixture from the first reactor to water in the second reactor generates a gas and the vent in the second reactor must be open. After transfer was completed, the agitator of the second reactor was stopped and the resulting two-phase system was allowed to separate for 30 minutes. The bottom organic phase was transferred from the second reactor and product recovered or sent to further processing. A sample is taken for analysis by vapor phase chromatograph.

In accord with the above procedure several runs were made and the results from Example 12 and the other runs are found in the Table III which follows.

TABLE III

| | | | Analysis of Acylated | | |
| | Starting | Weight of | 1-Methylpyrrole-2- | | Yield of |
| | 1-Methylpryrrole- | Acylated | acetonitrile by VPC, % | | 5-p-Toluoyl-1- |
| Example | 2-acetonitrile | Product, | 5-p-Toluoyl | 4-p-Toluoyl | Methylpyrrole-2- |
| No. | Purity, % | lbs | Isomer | Isomer | acetonitrile, % |
|---|---|---|---|---|---|
| 12 | 87.2 | 428 | 1410.0 | 6.6 | 63.0 |
| 13 | 84.5 | 384 | 16.7 | 8.1 | 69.6 |
| 14 | 84.5 | 401 | 15.7 | 7.13 | 68.3 |
| 15 | 84.5 | 395 | 15.2 | 7.25 | 65.1 |
| 16 | 84.5 | 405 | 16.4 | 8.33 | 72.2 |

Although the foregoing examples and the description have employed 1-methylpyrrole-2-acetonitrile to illustrate the process of this invention, other pyrrole derivatives show similar results. For instance, Example 17 illustrates the process of the invention when an alkylpyrrole-2-acetic acid ester is used as the starting pyrrole derivative. Accordingly, the process of the invention has applicability to a wide range of pyrrole derivatives. Particularly preferred pyrrole derivatives are selected from the group consisting of alkylpyrrole-2-acetonitrile and alkylpyrrole-2-acetic acid esters; most preferably, 1-methylpyrrole-2-acetonitrile and 1-methylpyrrole-2-acetic acid methyl ester. The following example is of course only illustrative and non-limiting.

EXAMPLE 17

To a reaction flask was added 10 grams of methylene chloride, 2.68 g (17.55 mmoles) of 1-methylpyrrole-2-acetic acid methyl ester and 2.71 g (17.53 mmoles) of p-toluoyl chloride at a temperature of −30° C. To this mixture was added 4.4 g of ethylaluminum dichloride as a 50 weight percent solution of methylene chloride. The mixture was slowly warmed to about 15° C. at which point reaction began with the evolution of ethane gas. Cooling was used to maintain the temperature of the reaction mixture at about 25°-30° C. After 0.5 hour reaction was completed there was added 3 ml of concentrated HCl and 3 ml of water to decompose unreacted catalyst with sufficient cooling to maintain the temperature at about 0° C. The bottom organic phase was separated. It weighed 13.22 g and was analyzed by NMR which indicated that the yield of 5-p-toluoyl-1-methylpyrrole-2-acetic acid methyl ester was 30.6 percent based upon the starting ester and the ratio of the 5-p-toluoyl isomer to 4-p-toluoyl isomer was 3.16.

What is claimed is:

1. A process for the preparation of 5-aroyl-pyrrole-2-acetic acid compounds, comprising the steps of mixing an aroyl halide selected from tolyoyl, benzoyl, p-chlorobenzoyl, thienoyl halide and such aroyl halides having the aromatic nucleus mono-, di-, or tri-substituted with groups selected from lower alkyl, halo, cyano, nitro, amino, lower alkoxy, methylthio and trifluoromethyl groups with a pyrrole compound having a group selected from cyano, carboxy, lower alkyl carboxylic acid ester, amide, lower alkyl substituted amide and dilower alkyl substituted amide groups attached in the 2-position to the pyrrole ring structure via a methylene group and adding a lower alkyl aluminum halide while maintaining the resultant mixture at a temperature of about 0° to about 40° C. whereby a 5-aroyl-pyrrole-2-acetic acid compound is produced.

2. The process of claim 1 wherein said pyrrole compound is 1-methylpyrrole-2-acetonitrile.

3. The process of claim 1 wherein said lower alkyl aluminum halide is a lower alkyl aluminum chloride.

4. The process of claim 1 wherein said lower alkyl aluminum halide is diethyl aluminum chloride.

5. The process of claim 1 wherein said lower alkyl aluminum halide is ethyl aluminum dichloride.

6. The process of claim 1 wherein said alkyl aluminum halide is ethyl aluminum sesquichloride.

7. The process of claim 1 wherein said aroyl halide is selected from the group consisting of toluoyl halide and benzoyl halide.

8. The process of claim 1 wherein said aroyl halide is p-toluoyl chloride.

9. The process of claim 1 further characterized in that said process is carried out in a reaction medium which is a lower alkyl halide.

10. The process of claim 9 in which said reaction medium is methylene chloride.

11. The process of claim 9 in which said reaction medium is 1,2-dichloroethane.

12. The process of claim 1 further characterized in that said process is carried out in monochlorobenzene as a reaction medium.

13. The process of claim 1 in which said pyrrole compound is 1-methylpyrrole-2-acetonitrile, said lower alkyl aluminum halide is diethyl aluminum chloride, said aroyl halide is p-toluoyl halide and said reaction temperature is from about 5 to about 25° C. and said process is carried out in a reaction medium which is methylene chloride.

14. The process of claim 1 further characterized in that the reaction is stopped after substantially all of said pyrrole compound is reacted by adding an alkyl aluminum halide decomposition agent selected from the group consisting of water, alcohol and dilute acid to the reaction mixture.

15. The process of claim 14 wherein said decomposition agent is water.

16. The process of claim 13 wherein the reaction is carried out for a period ranging from about 90 to about 120 minutes and then an amount of an alkyl aluminum halide decomposition agent selected from the group consisting of water, alcohol and dilute acid sufficient to decompose the remaining diethyl aluminum chloride is added to the reaction mixture and the 5-p-tolyoyl-1-methylpyrrole-2-acetonitrile is recovered from the reaction mixture.

17. The process of claim 1 in which said pyrrole compound is an alkylpyrrole-2-acetic acid ester in which said ester group is selected from emthyl, ethyl, propyl and butyl groups.

18. The process of claim 1 in which said pyrrole compound is an alkylpyrrole-2-acetic acid methyl ester.

19. The process of claim 1 in which said pyrrole compound is 1-methylpyrrole-2-acetic acid methyl ester.

20. The process of claim 1 in which said pyrrole compound is 1-methylpyrrole-2-acetic acid ethyl ester.

21. The process of claim 1 in which said pyrrole compound is an alkylpyrrole-2-acetic acid ester, said lower alkyl aluminum halide is ethyl aluminum dichloride, said aroyl halide is p-toluoyl halide, and said reaction temperature is from about 5 to about 25° C. and said process is carried out in methylene chloride as a reaction medium.

22. The process of claim 21 in which said alkylpyrrole-2-acetic acid ester is 1-methylpyrrole-2-acetic acid methyl ester and said p-toluoyl halide is p-toluoyl chloride.

23. A process for the preparation of 5-aroyl-pyrrole-2-acetic acid compounds, comprising the steps of mixing an aroyl halide selected from toluoyl, benzoyl, p-chlorobenzoyl, thienoyl halide and such aroyl halides having the aromatic nucleus mono-, di-, or tri-substituted with groups selected from lower alkyl, halo, cyano, nitro, amino, lower alkoxy, methylthio and trifluoromethyl groups with a pyrrole compound having a group selected from cyano, carboxy, carboxylic acid ester, amide lower alkyl substituted amide and dilower alkyl substituted amide groups attached in the 2-position to the pyrrole ring structure via a methylene group and a lower alkyl aluminum halide at a temperature below reaction temperature, warming the resultant mixture and maintaining said mixture at a temperature of from about 0° to about 40° C. whereby a 5-aroyl-pyrrole-2-acetic acid compound is produced.

* * * * *